United States Patent [19]

Nigro et al.

[11] Patent Number: 5,767,275
[45] Date of Patent: Jun. 16, 1998

[54] PREPARATION OF TRIAZOLONE COMPOUNDS

[75] Inventors: Alberto Nigro; Mauro Tomaselli, both of Rome, Italy

[73] Assignee: Aziende Chimiche Riunite Angelini Francesco A.C.R.A.F. S.p.A., Rome, Italy

[21] Appl. No.: 424,477

[22] PCT Filed: Nov. 6, 1993

[86] PCT No.: PCT/EP93/03119

§ 371 Date: May 11, 1995

§ 102(e) Date: May 11, 1995

[87] PCT Pub. No.: WO94/11357

PCT Pub. Date: May 26, 1994

[30] Foreign Application Priority Data

Nov. 13, 1992 [IT] Italy ................... MI92A2604

[51] Int. Cl.⁶ ................... C07D 403/04; C07D 249/12
[52] U.S. Cl. ................... 544/366; 548/263; 548/264.6
[58] Field of Search ............. 548/263.2, 264.6; 544/366

[56] References Cited

U.S. PATENT DOCUMENTS 3,514,466  5/1970  Stahle et al. ............ 548/263.2
3,857,845  12/1974 Palazzo .
4,338,317  7/1982  Temple, Jr. et al. .
4,596,884  6/1986  Madding .................. 548/263.2
5,094,683  3/1992  Daum et al. .................. 71/94

OTHER PUBLICATIONS

Davidson, "A Preparation of 3-amino-4,5-diaryl, etc" CA 91: 107946u (1979).
Gehlen et al. "1,2,4-triazolin-5-ones, etc" CA 61: 10674 a,b. (1964).
Senet et al, "Process for the preparation of etc" CA 111: 7413f (1989).
Cohen, "Preparation of some 3-hydroxy, etc" CA 89: 43256 (1978).
VEB Fahlberg-List, "Herbicidal Compositions, etc" C98: 174871 (1983).
Journal of Heterocyclic Chemistry, vol. 22, No. 4, pp. 1121-1125, G.D. Madding, et al. "Synthesis and X-Ray Crystal Structure of a 2,4,5-trisubstituted 1,2,4-triazol-3-one" (1985).

*Primary Examiner*—Patricia L. Morris
*Attorney, Agent, or Firm*—Oblon, Spivak, McClelland, Maier & Neustadt, P.C.

[57] ABSTRACT

Preparation of a 1,2,4-triazol-3-one compound substituted in positions 4 and 5 by an alkyl or aryl group and, optionally, in position 2 by an alkyl group, by reacting an ester a of carbamic acid N-substituted by an alkyl or aryl group with a hydrazide of an aliphatic or aromatic carboxylic acid, optionally N-substituted by an alkyl group, in the presence of a strong base.

12 Claims, No Drawings

PREPARATION OF TRIAZOLONE COMPOUNDS

DESCRIPTION

This is 371 of application of PCT/EP93/03119 filed Nov. 6, 1993.

This invention relates to a process for the preparation of triazoles.

More particularly, it relates to a process for the preparation of a 1,2,4-triazol-3-one compound substituted in the positions 4 and 5 by an alkyl or aryl group and optionally substituted in the position 2 by an alkyl group.

1,2,4-triazol-3-ones compounds bi-substituted in positions 4 and 5 or tri-substituted in positions 2, 4 and 5 are useful in themselves or as intermediates. Examples of the said compounds useful for human or animal therapy are described by U.S. Pat. No. 3,857,845 and U.S. Pat. No. 4,338,317.

Typical examples are ethoperidone and nefazodone.

The preparation of these compounds, however, implies a number of drawbacks.

U.S. Pat. No. 4,338,317 teaches to prepare the compounds of the formula:

where R is ethyl, R' is hydrogen or phenoxyethyl, and R" is 4-(halophenyl)-1-piperazinyl-propyl, by reacting an N-ethoxy-carboxyethiopropionamide of the formula:

where R and R' have the meanings set forth above, with a hydrazine compound of the formula:

where R" has the meanings set forth above.

However, this process presents a drawback in that during the reaction of compound (II) with compound (III) a highly toxic gas, i.e. hydrogen sulfide, is produced.

In addition, although the above-mentioned document states that the 1,2,4-triazol-3-one compounds tri-substituted in positions 2, 4 and 5 can be prepared directly from the compounds (II) wherein R' is not hydrogen, it does not disclose any examples of the preparation thereof.

In a subsequent document, G. D. Madding et al. (J. Het. Chem. 22, 1121–26, 1985) state that the said procedure is suitable only for preparing the intermediate compound bi-substituted in positions 2 and 5, from which the desired tri-substituted compound is then prepared by alkylation. Moreover, even though these Authors don't refer specifically to the production of hydrogen sulfide, they recognize the existence of "factors" which prompt to search for other synthesis pathways.

Then, G. D. Madding et al. (loc. cit.) describe two other routes for preparing bi-substituted intermediates from which the desired tri-substituted compound is prepared by alkylation.

The first route involves the cyclization in an alkaline medium of a semicarbazide of the formula:

where R' is phenoxyethyl and R is ethyl.

In turn the semicarbazide compound (IV) is obtained from an isocyanate compound of the formula:

where R' has the meanings set forth in connection with formula (IV), and a hydrazide compound of the formula:

where R has the meanings set forth in connection with formula (IV).

Hence, this synthesis has the drawback of using isocyanate compounds which are dangerous and toxic, particularly when they have a low molecular weight and are volatile.

On the other hand, through this pathway H. Gehlen et al. (Ann. 675, 180–188, 1964) had already prepared several compounds of formula I, in which the position 4 is substituted by an alkyl or aryl group and position 5 is substituted by an alkyl group.

However, to prepare the compounds which are tri-substituted in positions 2, 4 and 5, H. Gehlen et al. had to employ another method and the only substituent in position 2 was the phenyl group. Therefore, the tri-substituted compounds prepared by these Authors differ from the compounds which are intended to be prepared according to this invention.

The second route described by G. D. Madding et al. involves the cyclization in a basic medium of an N-carbomethoxyamidrazone compound of the formula:

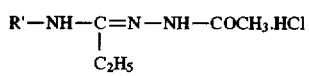

where R' is phenoxyethyl.

In turn, compound (VII) is prepared by reacting a compound of the formula:

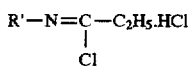

where R' is phenoxyethyl, with methyl carbazate and the compound of formula (VIII) is obtained by treating an amide of the formula:

where R' is phenoxyethyl, with phosgene.

Therefore, even in this case, a dangerous and toxic gas has to be employed.

Notwithstanding this drawback, the Authors regard this method as the most suitable for large-scale production.

The fact that such a complex process, which does not directly produce the desired tri-substituted compound and involves the use of a dangerous and toxic gas such as phosgene, is considered to be the best one among the methods investigated by the Authors points out the difficulties that the a person skilled in the art must face in the preparation of a compound of formula (I) where R and R' are alkyl or aryl and R" is hydrogen or alkyl.

Therefore, it is still needed a process suitable for directly yielding tri-substituted compounds without involving the use and/or the concurrent production of toxic and dangerous substances.

Surprisingly, it has now be found that this aim may be achieved by condensing a suitable ester of an N-substituted carbamic acid with an optionally N-substituted hydrazide of a carboxylic acid, in the presence of a strong base.

Therefore, it is an object of this invention to provide a process for preparing a 1,2,4-triazol-3-one compound substituted in positions 4 and 5 by an alkyl or aryl group and, optionally, in position 2 by an alkyl group, characterized in that an ester a of carbamic acid N-substituted by an alkyl or aryl group is reacted with a hydrazide of an aliphatic or aromatic carboxylic acid optionally N-substituted by an alkyl group, in the presence of a strong base.

Examples of suitable strong bases are the hydroxides and alcoholates of alkali metals and mixtures thereof, sodium hydride and sodium amide. Preferably, the alkali metal is sodium or potassium.

The reaction is preferably performed under conditions which allow to remove the water and alcohol as they form during the reaction. Examples of suitable conditions are, for example, the use of dehydrating agents and the heating to a temperature at which the volatile substances evaporate.

The reaction temperature is selected so as to prevent significant degradation of the reactants but at the same time complete the reaction quickly to reduce production times to an economic minimum. One of the most widely known and effective techniques to maintain both factors under control lies in the addition of a suitable diluent.

Therefore, the process of this invention is preferably carried out in the presence of a diluent and at a temperature of from −40° C. to 200° C.

When the strong base is sodium hydride, an alkali metal hydroxide, an alkali metal alcoholate or a mixture thereof, the diluent is preferably selected from those which are immiscible or very poorly miscible with water at their boiling temperature so that the water and alcohol which form during the reaction are removed as an azeotrope.

Examples of particularly suitable diluents for this step are aliphatic cyclic hydrocarbons such as methylcyclohexane and aromatic hydrocarbons such as toluene and xylene.

However, when the strong base is sodium amide, the reaction is preferably performed in the presence of liquid ammonia.

The process of this invention is preferably carried out by reacting, under the above-mentioned conditions, 1 mole of a carbamic acid ester of the formula:

R'—NH—COOY    (X)

where R' is alkyl or aryl, and
Y is $C_1-c_5$ alkyl,
with from 0.5 to 3 moles of a carboxylic acid hydrazide of the formula:

R"—NH—NH—CO—R    (XI)

where R" is hydrogen or alkyl, and
R is alkyl or aryl,
to yield a 1,2,4-triazol-3-one compound (I) where R, R' , R" have the meanings set forth above in connection with the compounds of formula (X) and (XI). As already mentioned, the reaction produces water and an alcohol of the formula YOH, where Y has the meaning set forth above connection with the compound of formula (X).

Preferred meanings of R, R' and R" according to this invention are as follows:

R is phenyl and $C_1-C_{10}$ alkyl optionally substituted by a phenyl group.

R' is phenyl, halophenyl and $C_1-C_{10}$ alkyl optionally substituted by phenyl or phenoxy.

R" is hydrogen and $C_1-C_{10}$ alkyl optionally substituted by an heterocyclic group.

Typical examples of R are phenyl, methyl, ethyl, propyl, isopropyl, hexyl and benzyl.

Typical examples of R' are phenyl, chlorophenyl, methyl, ethyl and phenoxyethyl.

Typical examples of R" are hydrogen and 4-(halophenyl)-1- piperazinyl-propyl.

The following examples are intended to illustrate the present invention without, however, limiting it in any way.

EXAMPLE 1

2 [3 [4-(3-chlorophenyl)-1-piperazinyl]propyl]-5-ethyl-4-(2-phenoxyethyl)-1,2,4-triazol-3-one (nefazodone) hydrochloride.

(Formula I: R=ethyl; R'=phenoxyethyl; R"=3 [4(3-chlorophenyl)-1-piperazinyl]propyl)

N-3[4-(3-chlorophenyl)-1-piperazinyl]-propyl-N'-propionyl-hydrazine (32.5 g; 0.1 moles) (prepared by reacting ethyl propionate with the N-3[4-(3-chlorophenyl)-1-piperazinyl]-propyl-hydrazine (U.S. Pat. No. 4,338,317 ) was dissolved in a solution of potassium hydroxide (6.6 g) in ethyl alcohol (40 ml). The solvent was removed by evaporation under reduced pressure.

To the thus obtained residue ethyl N-(2-phenoxyethyl)-carbamate, prepared as described in U.S. Pat. No. 3,320,302, (20.9 g; 0.1 moles) and xylene (50 ml) were added at 50° C. The reaction mixture was quickly heated under vigorous stirring to 135°–140° C. and maintained at this temperature for 4 hours while removing the distillate.

Water (100 ml) was added and then 37% hydrochloric acid up to pH 4. A heavy oil was formed which was recovered and taken up in isoamyl alcohol (100 ml).

The thus obtained solid product was recrystallised from 95% ethyl alcohol; m.p. 176°–177° C.

EXAMPLE 2

2[3[4-(3-chlorophenyl)-1-piperazinyl]propyl]-4,5-diethyl-1,2,4-triazol-3-one (ethoperidone) hydrochloride (Formula I: R=R'=ethyl; R"=3[4-(3-chlorophenyl)-1- piperazinyl]propyl).

The desired product was prepared following the same method as described in Example 1, except that the ethyl N-(2- phenoxyethyl)-carbamate (20.9 g; 0.1 moles) was substituted for N-ethyl-carbamate (17.6 g; 0.1 moles).

The thus obtained product melts at 201.5° C. (isopropanol).

EXAMPLE 3

5-ethyl-4-(2-phenoxyethyl)-1,2,4-triazol-3-one (Formula I: R'=$PhOC_2H_4$, R=$C_2H_5$, R"=H)

Propionyl hydrazine (53 g; 0.6 moles) was dissolved in a solution of potassium hydroxide (40 g) in ethyl alcohol (120 ml). The solvent was removed by evaporation under reduced pressure.

To the thus obtained residue ethyl N-(2-phenoxyethyl)-carbamate (105 g; 0.5 moles) and xylene (250 ml) were added at 50° C. The reaction mixture was quickly heated under vigorous stirring to 135° C. and maintained at this temperature for 4 hours while removing the distillate.

Xylene was completely removed by evaporation under reduced pressure. The residue obtained was taken up with water (250 ml) and the mixture heated to 80° C. and made acid with 37% hydrochloric acid up to pH 4. A solid was formed, which was recovered by filtration at 20° C., washed and then dried. 95.5 g of the desired product was thus obtained which, after recrystallization, melts at 136° C.

EXAMPLE 4

Working in a manner similar to that described in the previous examples the following products were prepared:
4,5-diphenyl-1,2,4-triazol-3-one; m.p. 160° C.
4-phenyl-5-benzyl-1,2,4-triazol-3-one; m.p. 261°–262° C.
4-phenyl-5-isopropyl-1,2,4-triazol-3-one; m.p. 168° C.
4-(4-chlorophenyl)-5-methyl-1,2,4-triazol-3-one; m.p. 172°–174° C.
4,5-diethyl-1,2,4-triazolone; m.p. 127°–129° C.
4-(2-chlorophenyl)-5-phenyl-1,2,4-triazol-3-one; m.p. 209° C.

We claim:

1. A process for preparing a 1,2,4-triazol-3-one compound of the formula:

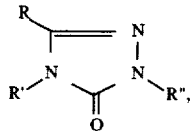

(I)

where R, R' and R" are defined below,
comprising reacting in the presence of a strong base:
(a) an ester of an N-substituted carbamic acid of the formula:

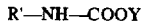 (X)

wherein
R' is phenyl, halophenyl or $C_1$–$C_{10}$ alkyl optionally substituted by phenyl or phenoxy; and
Y is $C_1$–$C_5$ alkyl; and
(b) a hydrazide of an aliphatic or aromatic carboxylic acid of the formula:

 (XI)

wherein
R is phenyl or $C_1$–$C_{10}$ alkyl optionally substituted by a phenyl group; and
R" is hydrogen, $C_1$–$C_{10}$ alkyl or 4-(halophenyl)-1-piperazinyl-propyl.

2. The process of claim 1, wherein said strong base is an alkali metal hydroxide, an alkali metal alcoholate, sodium hydride, sodium amide or a mixture thereof.

3. The process of claim 2, wherein said alkali metal is sodium or potassium.

4. The process of claim 1, wherein said reacting step is conducted at a temperature of –40° C. to 200° C. in the further presence of a diluent.

5. The process of claim 1, wherein said reacting step is conducted in the further presence of a diluent;
said strong base is sodium hydride, sodium hydroxide, potassium hydroxide, sodium alcoholate, potassium alcoholate or a mixture thereof; and
said diluent is immiscible or very poorly miscible with water at the boiling temperature.

6. The process of claim 5, wherein said diluent is methylcyclohexane, toluene, xylene or a mixture thereof.

7. The process of claim 1, wherein said reacting step is conducted in the further presence of a diluent;
said strong base is sodium amide; and
said diluent is liquid ammonia.

8. The process of claim 1, wherein R' is phenyl, chlorophenyl, methyl, ethyl or phenoxyethyl.

9. The process of claim 1, wherein R" is hydrogen or 4-(halophenyl)-1-piperazinyl-propyl.

10. The process of claim 1, wherein R is phenyl, methyl, ethyl, propyl, isopropyl, hexyl or benzyl.

11. The process of claim 4, wherein said strong base is sodium hydride, sodium hydroxide, potassium hydroxide, sodium alcoholate, potassium alcoholate, or a mixture thereof; and
said diluent is immiscible or very poorly miscible with water at said temperature.

12. The process of claim 4, wherein said strong base is sodium amide and said diluent is liquid ammonia.

* * * * *